United States Patent [19]

Campbell et al.

[11] Patent Number: 4,503,307

[45] Date of Patent: Mar. 5, 1985

[54] SHIELDING APPARATUS FOR MICROWAVE THAWING

[75] Inventors: Nancy L. Campbell; John G. Pinto; John A. Drewe; Patrick D. Hayes, all of San Diego; Nelson Robert A., La Mesa, all of Calif.

[73] Assignee: The United States of America as represented by the Secretary of the Navy, Washington, D.C.

[21] Appl. No.: 505,584

[22] Filed: Jun. 20, 1983

[51] Int. Cl.³ .................. H05B 6/64; A61M 1/03
[52] U.S. Cl. .............. 219/10.55 E; 219/10.55 R; 219/10.55 F; 604/403
[58] Field of Search .......... 219/10.55 F, 10.55 E, 219/10.55 M, 10.55 R; 128/214 A; 604/403, 408

[56] References Cited

U.S. PATENT DOCUMENTS

| | | | |
|---|---|---|---|
| 3,427,422 | 2/1969 | Müller | 219/10.55 R |
| 3,436,506 | 4/1969 | Smith | 219/10.55 F |
| 3,941,967 | 3/1976 | Sumi et al. | 219/10.55 |
| 4,046,983 | 9/1977 | Ishino et al. | 219/10.55 |
| 4,122,324 | 10/1978 | Falk | 219/10.55 |
| 4,336,435 | 6/1982 | Kashyap et al. | 219/10.55 F |
| 4,362,917 | 12/1982 | Freedman et al. | 219/10.55 E |
| 4,398,077 | 8/1983 | Freedman et al. | 219/10.55 E |

Primary Examiner—Roy N. Envall, Jr.
Assistant Examiner—M. M. Lateef
Attorney, Agent, or Firm—Robert F. Beers; Ervin F. Johnston; Thomas Glenn Keough

[57] ABSTRACT

A shielding apparatus is provided for containing frozen bags of fluid and more particularly for containing frozen bags of blood components during microwave thaw. The apparatus includes a metal box for receiving a blood bag, the box having a bottom and sides. A metallic lid is provided, and a hinging device pivotally mounts the lid to the box for enclosing the blood bag therein. The lid and optionally the bottom of the box may be provided with an aperture for allowing microwaves to enter the box. Radiation absorbing strips are mounted along the edges of the apertures for absorbing E field reflections toward the blood bag. The apertures allow microwave energy to be concentrated in the more voluminous part of the blood bag while the edges of bag as well as any tubing are shielded by the metallic box. This apparatus prevents boiling of the blood in the lower volume areas of the bag.

6 Claims, 11 Drawing Figures

SHIELDING APPARATUS FOR MICROWAVE THAWING

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

A standard microwave oven has been modified to enable rocking movement of a frozen bag of blood components during microwave thaw. With such a modified oven the warmer thawed portions of blood components flow over the frozen portions so as to distribute heat and minimize boiling of the blood components. It has been found however, that even with the rocking movement boiling of the blood can take place in the minimal areas of the bag of blood components such as the edges and in the tubular portions thereof. Various shielding devices have been used as microwave blood warmers in standard mirowave ovens. These shielding devices have been tested and found incapable of providing complete protection for the bag of blood components. Further, these shielding devices were found to be more difficult to use.

STATEMENT OF THE INVENTION

The present invention provides a shielding apparatus for optimum protection of a frozen bag of blood components during microwave thaw. This has been accomplished by providing a metal box for receiving the bag of blood components, the box having a bottom and sides. A metallic lid is provided, and a hinge device pivotally mounts the lid to the box for enclosing the blood bag therein. The lid and optionally the bottom of the box have an aperture for allowing microwaves to enter the box at the central more voluminous portion of the blood bag. A radiation absorbing strip is mounted along the edge of each of the apertures for absorbing E field reflections toward the blood bag. Insulation may be mounted along the edges of the lid for preventing arcing between the lid and the box. The hinges and the box may be specially adapted to enable the lid to recess into the box so as to snugly retain the blood bag therein. This snug arrangement prevents the microwave energy from heating the shielded tubes and circumference of the bag. When this shielding apparatus is used in combination with the modified microwave oven frozen bags of blood components can be thawed during pulsed application of the microwave energy without any danger of overheating of the blood.

OBJECTS OF THE INVENTION

An object of the present invention is to provide an improved shielding apparatus for frozen bags of blood components during microwave thaw.

Another object is to provide a microwave thaw shielding apparatus which is easy to use and which will provide improved protection for frozen bags of blood components.

A further object is to provide a shielding apparatus for frozen blood bags which can be utilized in combination with a modified microwave oven which rocks the bag to obtain heat distribution.

Still another object is to provide a shielding apparatus which snugly contains frozen blood bags and which allows microwaves to enter only a central portion of the bag without any E field reflections.

These and other objects of the invention will become more readily apparent from the ensuing specification when taken together with the drawings.

DESCRIPTION OF THE PREFERRED EMBODIMENT

Figure 1:
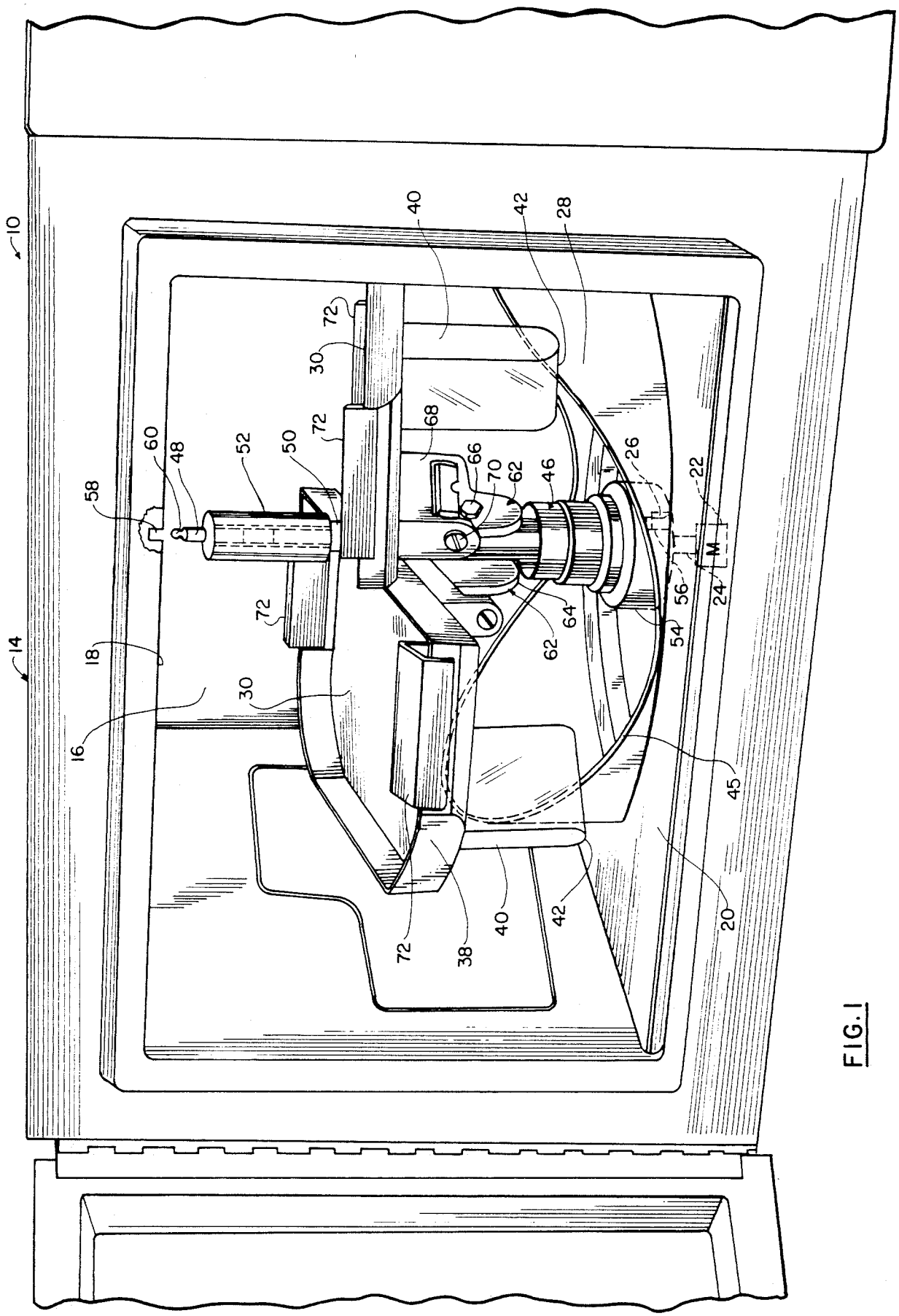
FIG. 1 is a perspective view of an apparatus to be used with the present invention for heating contained liquid or thawing frozen bags of blood components with portions cut away to illustrate various details thereof.
Figure 2:
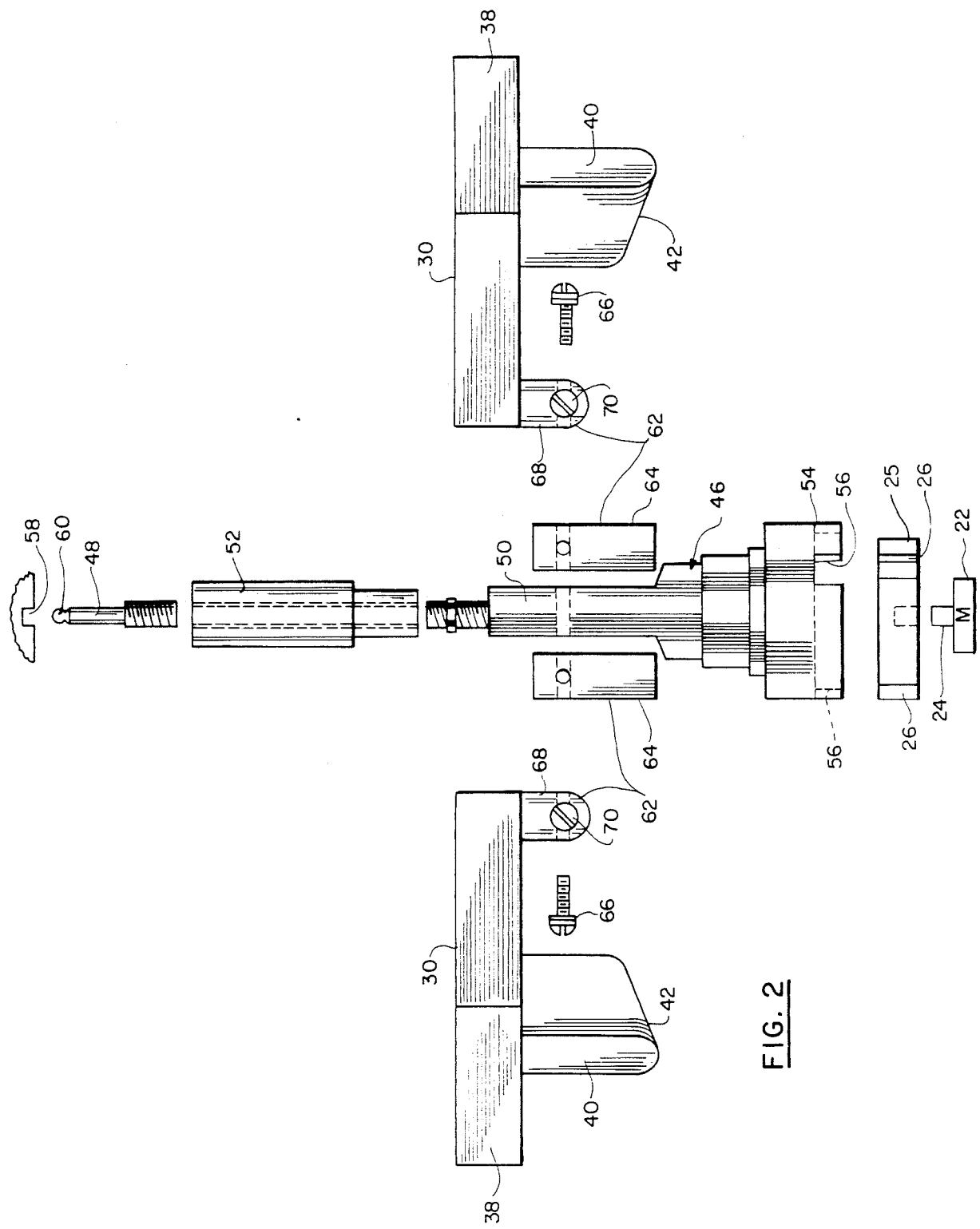
FIG. 2 is an exploded view of part of the mechanism utilized within the microwave oven.
Figure 3:
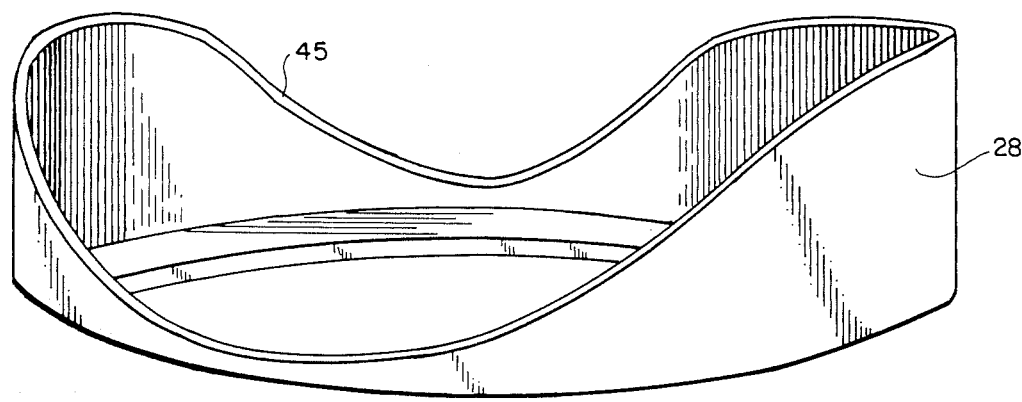
FIG. 3 is a perspective view of the track which is utilized in the heating apparatus.
Figure 4:
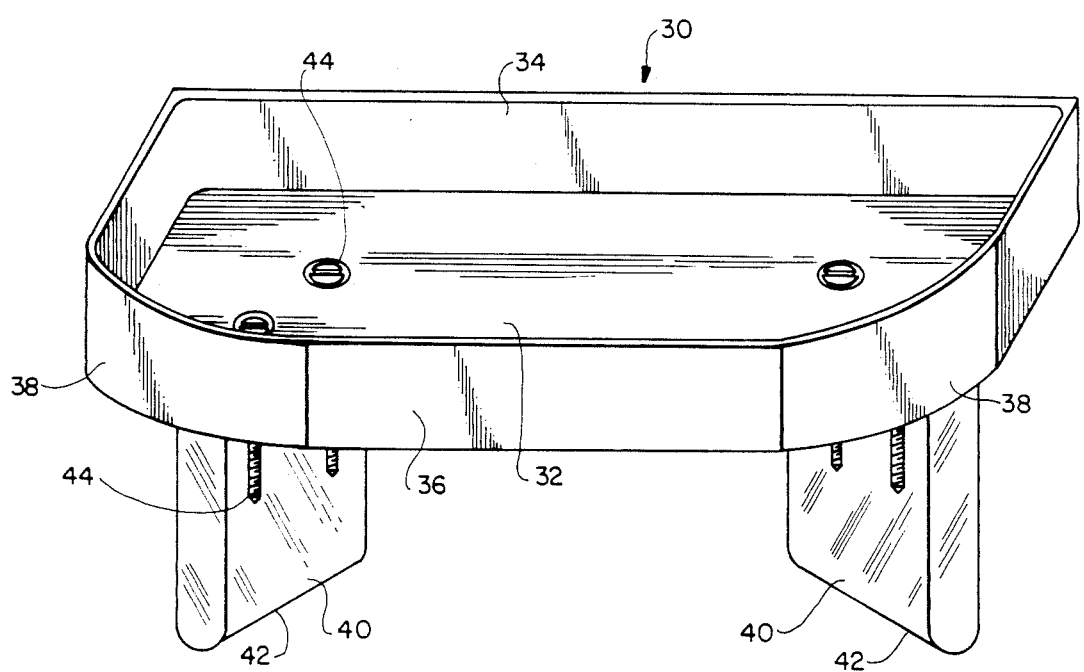
FIG. 4 is a perspective view of a tray utilized in the heating apparatus.
Figure 5:
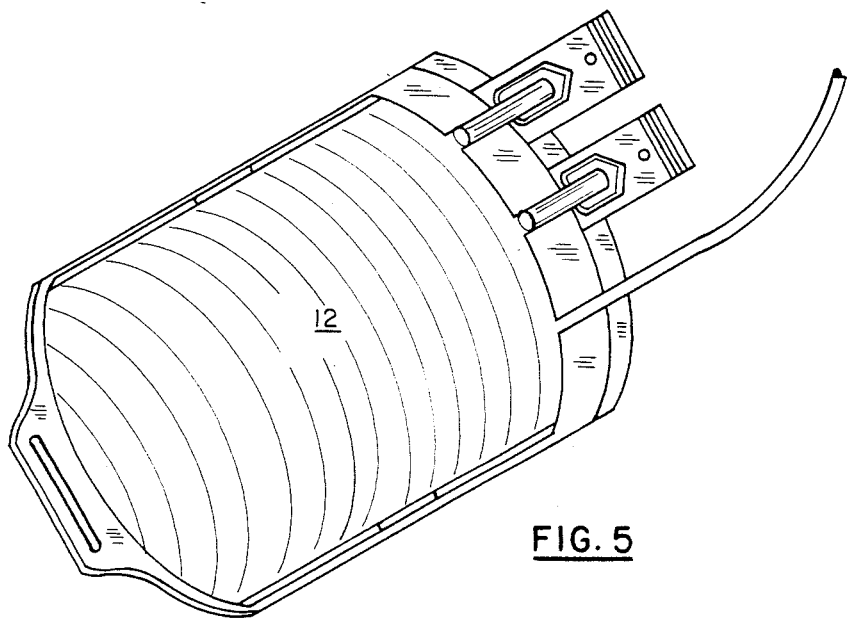
FIG. 5 is a perspective view of a bag of frozen blood components.

Referring now to the drawings wherein like reference numerals designate like or similar parts throughout the several views there is illustrated in FIG. 1 a heating apparatus 10 which is to be used in conjunction with the present invention for heating contained liquid, and more particularly for thawing frozen bags of blood components, one such bag being shown at 12 in FIG. 5. The heating apparatus 10, which is shown in FIGS. 1–4, will be described prior to the description of the present invention, which is shown in FIGS. 6–11, since the heating apparatus 10 is necessary for the utilization of the present invention for thawing a bag of blood components. The heating apparatus 10 includes a standard carousel microwave oven 14 which is available from Sharp. The microwave oven has a cavity 16 for receiving objects to be heated, the cavity having a top and a bottom which are defined by an oven ceiling 18 and an oven floor 20 respectively. The Sharp manufactured microwave oven has a motor 22 which is located in the oven below the oven floor 20. As shown in FIGS. 1 and 2, the motor has a shaft 24 which extends upwardly into the oven cavity 16 and is attached to a coupler 25 (see FIG. 2) with outwardly extending projections 26. In the standard Sharp microwave oven a flat plate (not shown) rests upon the coupler 25, and the projections 26 of the coupler bear against lands in the bottom of the plate for rotating the plate during operation of the oven. This plate is not utilized in the present invention, and is therefore removed so that the apparatus of the invention can be inserted in the oven for the specialized heating purposes of the invention.

A track 28 is mounted in the oven cavity and has a peak and a valley with respect to the oven floor 20. The track, which is shown in more detail in FIG. 3, is preferably a circular ring with a plurality of peaks and valleys with respect to the oven floor. The track 28 is constructed of a microwave transparent material, such as plexiglass or polypropylene, and may be fixed in place to the oven floor 20 centrally about the motor shaft 24 by any suitable means such as epoxy cement.

As illustrated in FIG. 1 a pair of trays 30 may be provided, each tray being capable of receiving an object to be heated. As illustrated in FIG. 4, the tray 30 may have a substantially flat bottom 32 and inner and outer sides 34 and 36. Outside corners 38 are rounded for a purpose to be explained hereinafter. The tray 30 has a pair of downwardly extending projections 40 with bottom rounded edges 42. The projections 40 are mounted to the bottom of the tray 30 by any suitable means such as plastic screws 44, and are angled with respect to the tray for a purpose which will be explained in more detail hereinafter. The projections 40 are made of a microwave transparent material, preferably plexiglass or polypropylene.

Means are provided for pivotally supporting the trays 30 within the oven cavity 16 with each tray in engagement with the track 28. In the preferred embodiment the bottom rounded edges 42 of the downwardly extending projections 40 engage the top rim 45 of the track 28. As illustrated in FIGS. 1 and 2 the pivotal support means may include a shaft 46 which has top and bottom portions 48 and 50 which are threaded into a coupler 52 so that the shaft 46 can be lengthened or shortened for proper operation within the oven. The bottom of the bottom shaft section has an enlarged hollow portion 54 with cutouts 56 (one cutout being shown in the drawings) for receiving the projections 26 of the coupler (one such projection being shown in the drawings) which is attached to the motor shaft 24. When the motor 22 is operated the coupler 25 will rotate the shaft 46 within the oven cavity 16. The ceiling 18 of the standard Sharp microwave oven is provided with a hole 58 for receiving a temperature probe (not shown) which is not utilized in this invention. The top of the top shaft portion 48 is provided with a ball extension 60 which is slidably received within the hole 58 when the shaft 46 is sufficiently lengthened by means of the threaded coupler 52. When the ball extension 60 is received within the ceiling hole 58 the shaft 46 is secured in a substantially upright position, as illustrated in FIG. 1.

In the preferred embodiment the pivotal supporting means includes a universal joint 62 for connecting each tray 30 to the shaft 46 at a position above the track 28. (See FIGS. 1 and 2). Each universal joint may include a hub 64 which is rotatably connected to a respective side of the shaft 46 by any suitable means such as a pin or bolt 66. The universal joint further includes a yoke 68 which is secured to the bottom of the tray 30 adjacent its inner edge and which is pivotally connected to the hub 64 by any suitable means such as a pin or bolt 70. With this arrangement each tray can be rocked back and forth in two directions with respect to a horizontal plane when the shaft 46 is rotated by the motor 22. This rocking action is enabled by the camming action of the track 28 on the downwardly extending tray projections 40. In order to provide for an optimum and efficient camming action during rotation the downwardly extending projections 40 extend radially from the shaft 46. With this arrangement the bottom curve 42 of each projection 40 meets the top rim 46 of the track 28 in a square fashion.

Means are located within the oven for imparting relative rotation between the trays 30 and the track 28. In the preferred embodiment this relative rotation imparting means imparts rotation of the trays 30 with respect to the track 28, however it is to be understood that in a broader conception of the invention the shaft 46 could be maintained stationary while the track 28 is rotated thereunder. In The preferred embodiment the relative rotation imparting means includes the motor 22 which is connected to the shaft 46 via the coupler 25.

The size of the trays 30 is optimized by the rounded corners 38, which are shown in FIG. 4 and which were mentioned hereinabove. When the trays are rotated the rounded corners 38 enable the tray to clear the sides within the oven cavity. In order to secure objects of various sizes within a tray 30 U-shaped inserts 72 of various sizes are provided which straddle the sides of a respective tray.

The heating apparatus 10 is especially adapted for thawing frozen bags of blood components, such as the frozen bag of blood components 12 shown in FIG. 5. It is extremely important that the blood not boil due to high concentrations of microwave energy. The problem areas in the blood bag are around the edges and the tubing extending from the bag where less volume of the blood is located. The tendency is for the blood at the edges of the bag to heat up and even boil while the larger volume of blood at the center of the bag remains frozen. The rocking movements of the bag in the heating apparatus 10 ensures optimum flow of the heated portions of the blood over the frozen portions thereof.

Figure 6:
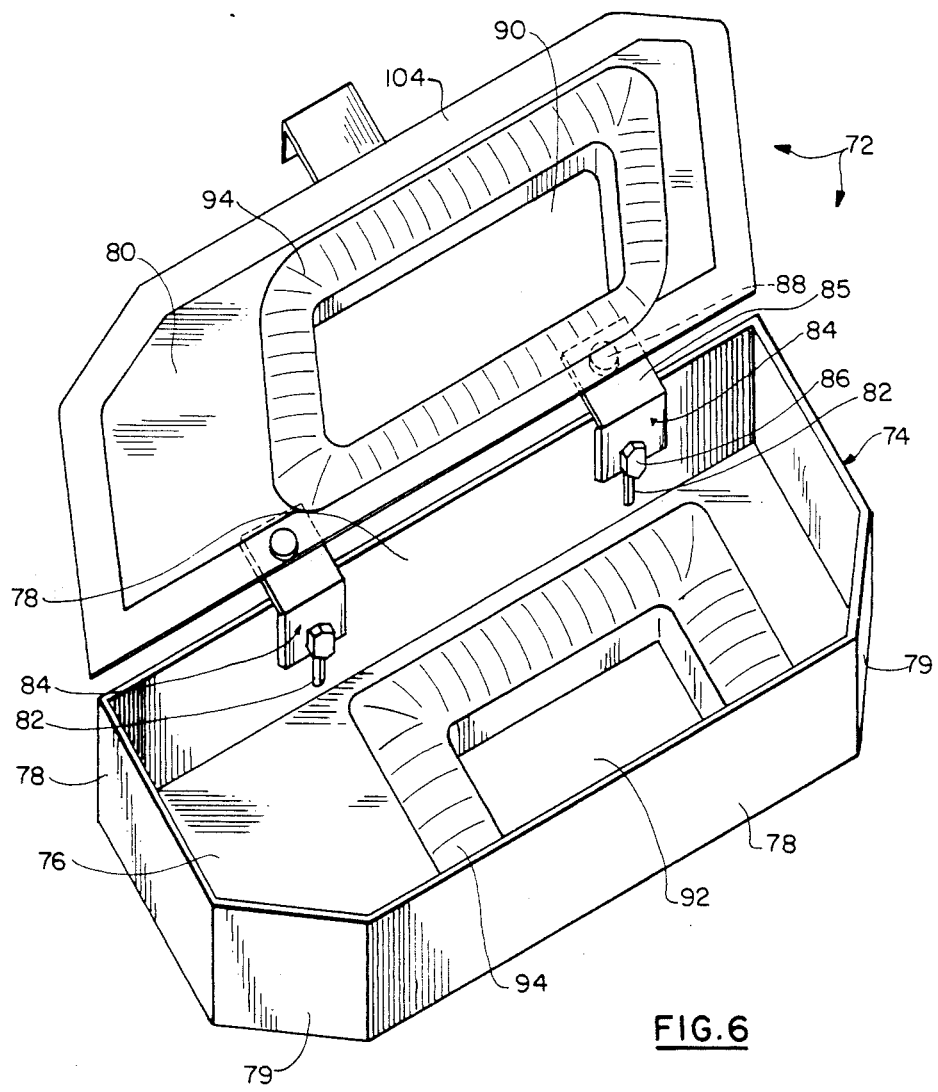
FIG. 6 is a perspective view of the apparatus of the present invention to be used for containing frozen blood bags during microwave thaw.
Figure 10:
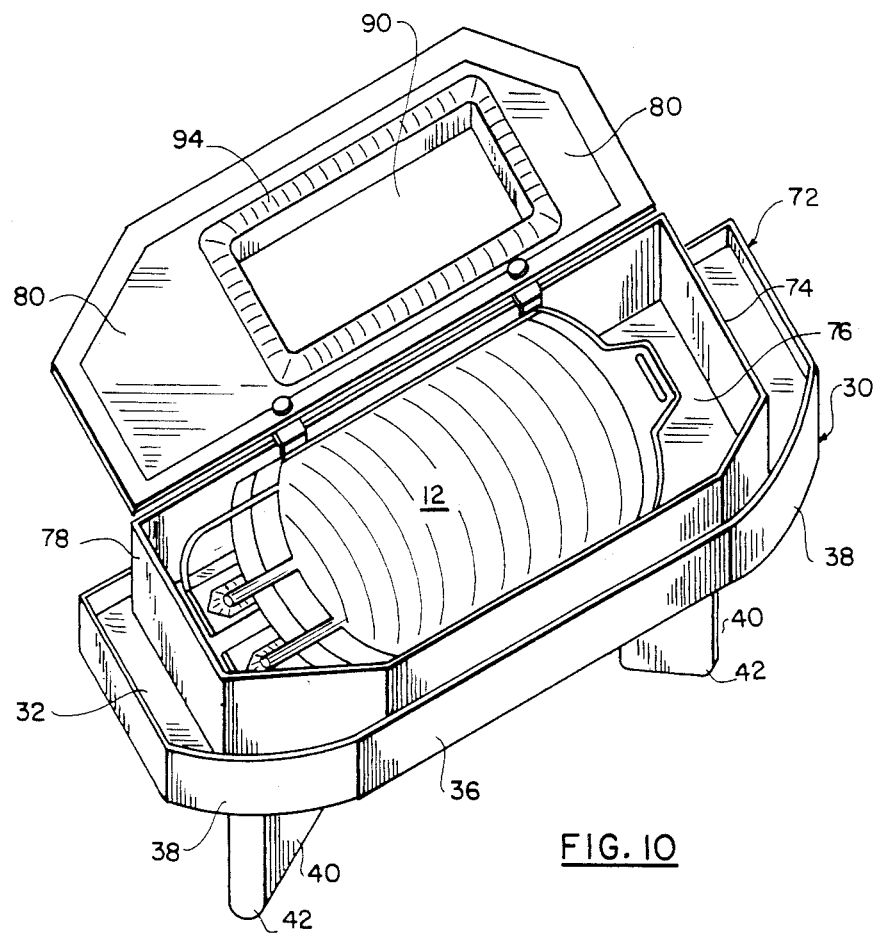
FIG. 10 is a perspective view of a frozen bag of blood within the container box of FIG. 6, which box is laying within the tray of FIG. 3.

For highly efficient use of the heating unit 10 it is desirable to shield the edges of the blood bag 12 from microwave energy while allowing the microwave energy to penetrate the center more voluminous portion of the blood bag. This has been accomplished by providing the present invention which is an apparatus 72, as shown in FIG. 6, for containing the frozen blood bag 12, this apparatus being utilized with the microwave oven and apparatus shown in FIGS. 1–4. The containing apparatus 72 may include a metallic box 74 which is capable of receiving the blood bag 12, as shown in FIG. 10. As shown in FIG. 6, the container apparatus 72 has a bottom 76 and sides 78 with the sides being angled at the front at 79. A metallic lid 80 is provided, and hinge means 84 are provided for pivotally mounting the lid to the box for closing the blood bag 12 therein.

Figure 9:
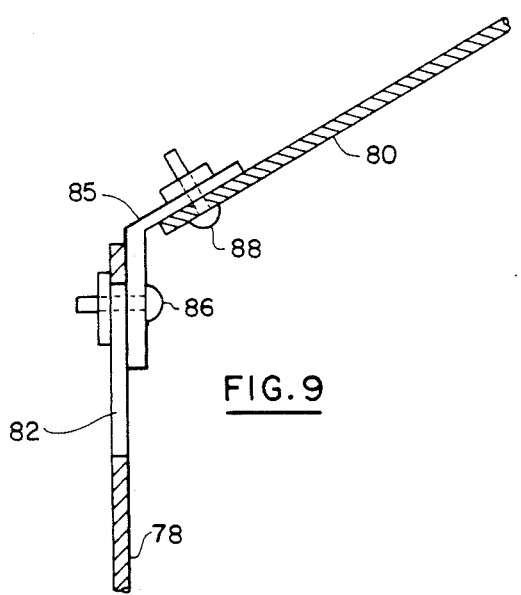
FIG. 9 is a side cross-sectional view of the hinge which supports the lid to the box of the container apparatus of FIG. 6.
Figure 11:
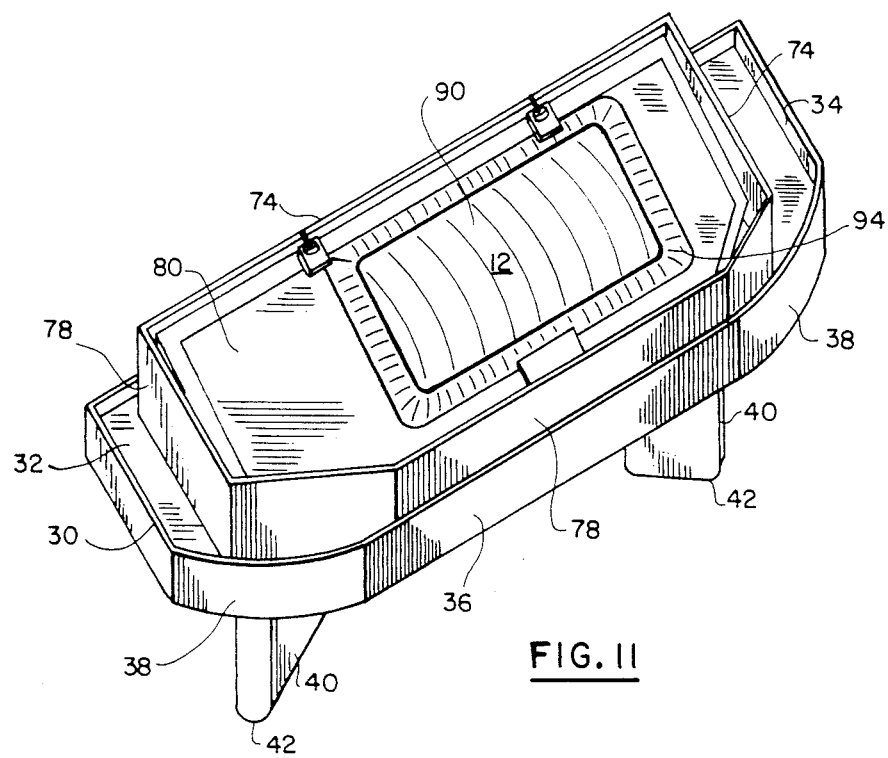
FIG. 11 is the same as FIG. 10 except the lid of the container box is closed.

As shown in FIGS. 6 and 9, the hinge means 84 may include on side of the box 74 having a plurality of vertical slots 82. A plurality of hinges 85 are mounted in the slots 82 and are adjustable up and down therein to various positions. As illustrated in FIG. 9, this may be accomplished by a bolt nut combination 86 which extends through a respective hinge 85 and slot 82. Each hinge 85 may be connected to the edge of the lid 80 by a bolt and nut combination 88. The hinge 85 is constructed of a microwave transparent insulative material, and is preferably a plastic strap which will bend along its center portion. In the preferred embodiment the bolt and nut combinations 86 and 88 are also made of plastic. With this arrangement the lid 80 can be selectively recessed within the box 74 for snugly containing the blood bag 12, as illustrated in FIG. 11.

Figure 7:
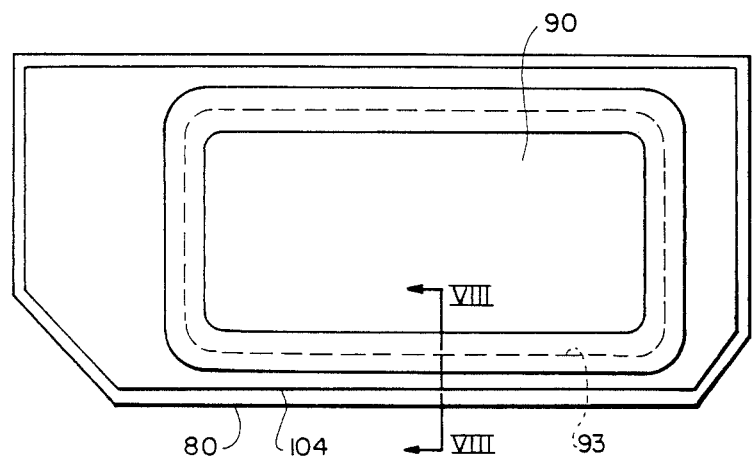
FIG. 7 is a bottom view of the lid of the container apparatus of FIG. 6.
Figure 8:
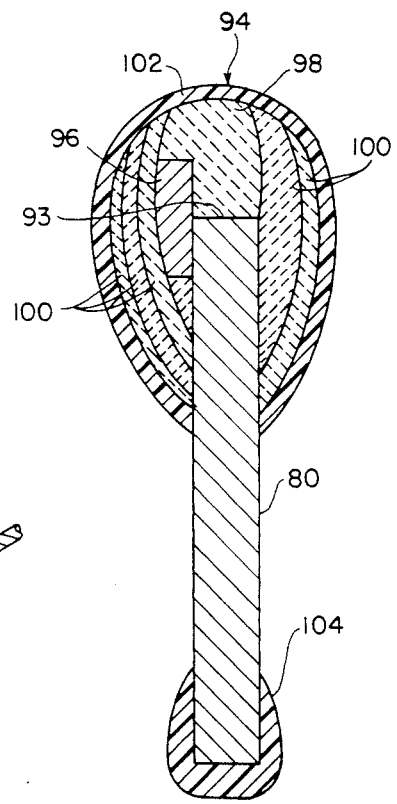
FIG. 8 is a view taken along plane VIII—VIII of FIG. 7 with the details somewhat enlarged for illustration purposes.

As shown in FIGS. 6 and 7 the lid 80 is provided with a central aperture 90 for allowing microwaves to enter the box. It should be noted that the central location of this aperture will allow the microwaves to penetrate the more voluminous portion of the blood components in the central portion of the bag 12. In a like manner the bottom 76 of the box may be provided with a central aperture 92 which is substantially opposite the lid aperture 90 when the lid is closed. The edge of each aperture 90 and 92 is provided with radiation absorbing means 94 for absorbing E field reflections toward the bag, the edge of the lid aperture being shown at 93 in FIGS. 7 and 8. As shown in FIGS. 7 and 8 the radiation absorbing means 94 may include a ring of microwave absorbing material 96 which extends along the peripheral side of the lid aperture closest to the blood component bags. The microwave absorber ring 96 has a width which extends perpendicularly both ways from the edge 93 so as to absorb the E field of microwave energy which is generated along the edge 93 of the aperture.

Means are provided for thermally insulating the ring 96 of absorbing material from the blood bag 12. The thermal insulation means may include a ceramic adhesive 98 which extends between the aperture edge 93 and the ring 96 of absorbing material. Layers of ceramic paper 100 may be laid over the ring of absorbing material 96 and the ceramic adhesive 98 on both sides thereof, and may itself be held in place by ceramic adhesive. A plastic coating 102 may encapsulate the entire assembly to the lid, as shown in FIG. 8. Also, as shown in FIGS. 7 and 8, the entire outer edge of the lid 80 may be coated with several layers of plastic 104. This plastic coating will prevent arcing of the outer edge of the lid to the metallic box 74 when the lid 80 is closed and the assembly is subjected to microwave energy.

FIG. 10 illustrates the blood component bag 12 received within the container apparatus 72, and the container apparatus 72, in turn, received within one of the trays 30. When the lid 80 of the container apparatus is closed into the box 74 (see FIG. 11) the tray is readied for rocking and rotative motions within the microwave oven, as illustrated in FIG. 1. When the trays 30 are loaded with the blood bags 12 is closed containers 72 and then rocked and rotated within the oven 10 the melted portions of the blood components flow over the frozen portions to distribute heat, and the apertures 90 and 92 in the containers 72 will allow heat to penetrate the more voluminous central portions of the blood bags 12. With these combined apparatuses frozen blood bags can be rapidly and efficiently thawed for preparing blood for human use.

Obviously, many modifications and variations of the present invention are possible in the light of the above teachings. It is therefore to be understood that within the scope of the appended claims the invention may be practiced otherwise than as specifically described.

What is claimed is:

1. A shielding apparatus for containing frozen blood bags during microwave thaw comprising:
   a metallic box for receiving a blood bag, the box having a bottom and sides;
   a metallic lid;
   hinge means pivotally mounting the lid to the box for enclosing the blood bag therein the hinge means including:
   a plurality of vertical slots in a side of the box;
   a plurality of hinges mounted in the slots and adjustable up and down in the slots to various positions; and
   means connected to the hinges for fixing the positions of the hinges in the slots; and
   the lid having an aperture for allowing microwaves to enter the box and thaw the blood in the blood bag.

2. An apparatus as claimed in claim 1 including:
   radiation absorbing means mounted along the edge of the lid aperture for absorbing E field reflections toward the blood bag;
   the bottom of the box having an aperture for allowing microwaves to enter the box; and
   radiation absorbing means mounted along the edge of the box aperture for absorbing E field reflections toward the blood bag.

3. An apparatus as claimed in claim 2 including:
   thermal insulation means mounted along the radiation absorbing means for insulating the radiation absorbing means from the blood bag.

4. An apparatus as claimed in claim 1 including:
   electrical insulation means mounted along the edges of the lid.

5. An apparatus as claimed in claim 4 including:
   the hinges being constructed of microwave transparent material.

6. A shielding apparatus for containing frozen blood bags during microwave thaw comprising:
   a metallic box for receiving a blood bag, the box having a bottom and sides;
   a metallic lid;
   hinge means pivotally mounting the lid to the box for enclosing the blood bag therein, the hinge means including:
   a plurality of vertical slots in a side of the box;
   a plurality of hinges mounted in the slots and adjustable up and down in the slots to various positions; and
   means connected to the hinges for fixing the position of the hinges in the slots so that the lid can be selectively recessed in the box for snugly containing the blood bag;
   the lid having an aperture for allowing microwaves to enter the box;
   radiation absorbing means mounted along the edge of the lid aperture for absorbing E field reflections toward the blood bag;
   the bottom of the box having an aperture for allowing microwaves to enter the box;
   radiation absorbing means mounted along the edge of the box aperture for absorbing E field reflections toward the blood bag;
   the radiation absorbing means including:
   a ring of microwave absorbing material along one peripheral side of the lid aperture;
   the microwave absorber ring having a width which extends perpendicularly both ways from the peripheral side of the lid aperture; and
   means for thermally insulating the ring of absorbing material from the blood, the thermal insulating means including:
   ceramic adhesive extending between the aperture edge and the ring of absorbing material; and
   layers of ceramic paper over the ring of absorbing material and the ceramic adhesive; and
   a plastic coating over the ceramic paper; and
   insulation means mounted along the edges of the lid.

* * * * *